United States Patent [19]

Panagiotopulos

[11] 4,383,531
[45] May 17, 1983

[54] COMPACT HYGIENIC SYRINGE APPARATUS

[76] Inventor: Panagiotis Panagiotopulos, 25279 Ironwood Ct., Hayward, Calif. 94545

[21] Appl. No.: 339,768

[22] Filed: Jan. 15, 1982

[51] Int. Cl.³ .............................................. A61M 1/00
[52] U.S. Cl. .................................. 604/114; 604/135
[58] Field of Search ............... 128/230, 229, 234, 251, 128/224

[56] References Cited

U.S. PATENT DOCUMENTS

| | | | |
|---|---|---|---|
| 1,494,985 | 5/1924 | Beck | 128/230 |
| 1,973,262 | 9/1934 | McQueen, Jr. | 128/229 |
| 2,283,848 | 5/1942 | Chapin | 128/229 |

FOREIGN PATENT DOCUMENTS

| | | | |
|---|---|---|---|
| 328176 | 4/1918 | Fed. Rep. of Germany | 128/234 |
| 348621 | 2/1922 | Fed. Rep. of Germany | 128/234 |
| 147284 | 5/1931 | Switzerland | 128/234 |

*Primary Examiner*—John D. Yasko
*Attorney, Agent, or Firm*—Linval B. Castle

[57] ABSTRACT

A portable, compact, hygienic syringe apparatus employing a rigid transparent canister divided into upper and lower sections, each having a closeable cover. The lower section houses a flexible self-coiling tubing having one end releasably connected through a floor section into the upper fluid-containing section. A spring-loaded piston in the upper section is latched up while fluid is poured into that section. When the latch is released, the spring-loaded piston forces the fluid through the tubing.

13 Claims, 2 Drawing Figures

COMPACT HYGIENIC SYRINGE APPARATUS

BRIEF SUMMARY OF THE INVENTION

This invention relates to a hygienic syringe apparatus and in particular to a novel enema or douche apparatus comprising a spring-driven fluid pump and self-recoiling tubing in a portable, convenient and nonconspicuous wall mountable canister.

The conventional gravity-fed fountain syringes for personal hygiene have functioned satisfactorily for many years but have also proven to be a great inconvenience. Because it is unsightly and has an appearance that suggests immodesty, the conventional enema or douche bag is usually hidden in a closed storage cabinet and brought out when necessary, filled, and then hung from a shower curtain rod, conventionally located hook, or towel bar. The prior art fountain syringes are typically made of a pliable rubber or rubber-like material that cannot be opened for inspection and cleaning, and the inner surfaces of such devices may become unknowingly contaminated.

The syringe apparatus of this invention is entirely contained in a closed tubular canister that is mountable in a socket that may be attached to a convenient wall location. Because the canister is completely closed when not in use, it is quite inconspicuous and may be mistaken for a powdered soap dispenser, air purifier, or the like. When the apparatus is to be used, the hinged top cover is opened, a spring-loaded piston is lifted to its full extent and the attached handle is rotated a quarter turn to latch the piston in a bayonet type lock. The desired fluid is then poured into a one-way funnel molded into the top surface of the piston and into a cylindrical reservoir which may contain electrical heating elements and which is located beneath the raised piston. A port in the reservoir floor, which is located at about the center of the canister, interconnects the fluid cylinder with one end of a retractable, coiled, flexible tubing which may be removed for use after unlatching a hinged bottom cover on the canister. The syringe, now ready for use, is turned on by re-rotating the piston handle to unlatch the bayonet lock. The spring then forces the piston toward the floor of the reservoir to force the fluid contained therein through the tubing, an open valve, and a disposable syringe fitting at the tubing end. When the enema or douche has been completed, the apparatus may be cleaned or rinsed by refilling with a suitable detergent and/or rinse, and the spring-loaded cylinder again released to flush the cylinder and retractable hose.

Briefly described, the syringe apparatus of the invention comprises a tubular canister having a sealed internal partition forming a reservoir floor near the center of the canister and with hinged covers at each end of the canister. The cylindrical reservoir is connected through a port in the floor to a flexible self-retracting fluid dispensing tubing. A piston in the cylinder portion above the floor is spring-loaded and, after opening the top cover of the canister, may be lifted and latched to provide a space for fluid which is admitted into the reservoir through a check valve in the piston. Release of the piston latch will cause the spring-loaded piston to compress against the fluid and force it through the dispensing tubing.

BRIEF DESCRIPTION OF THE DRAWINGS

In the drawings which illustrate a preferred embodiment of the invention.

DETAILED DESCRIPTION OF THE PREFERRED EMBODIMENT

Figure 1:
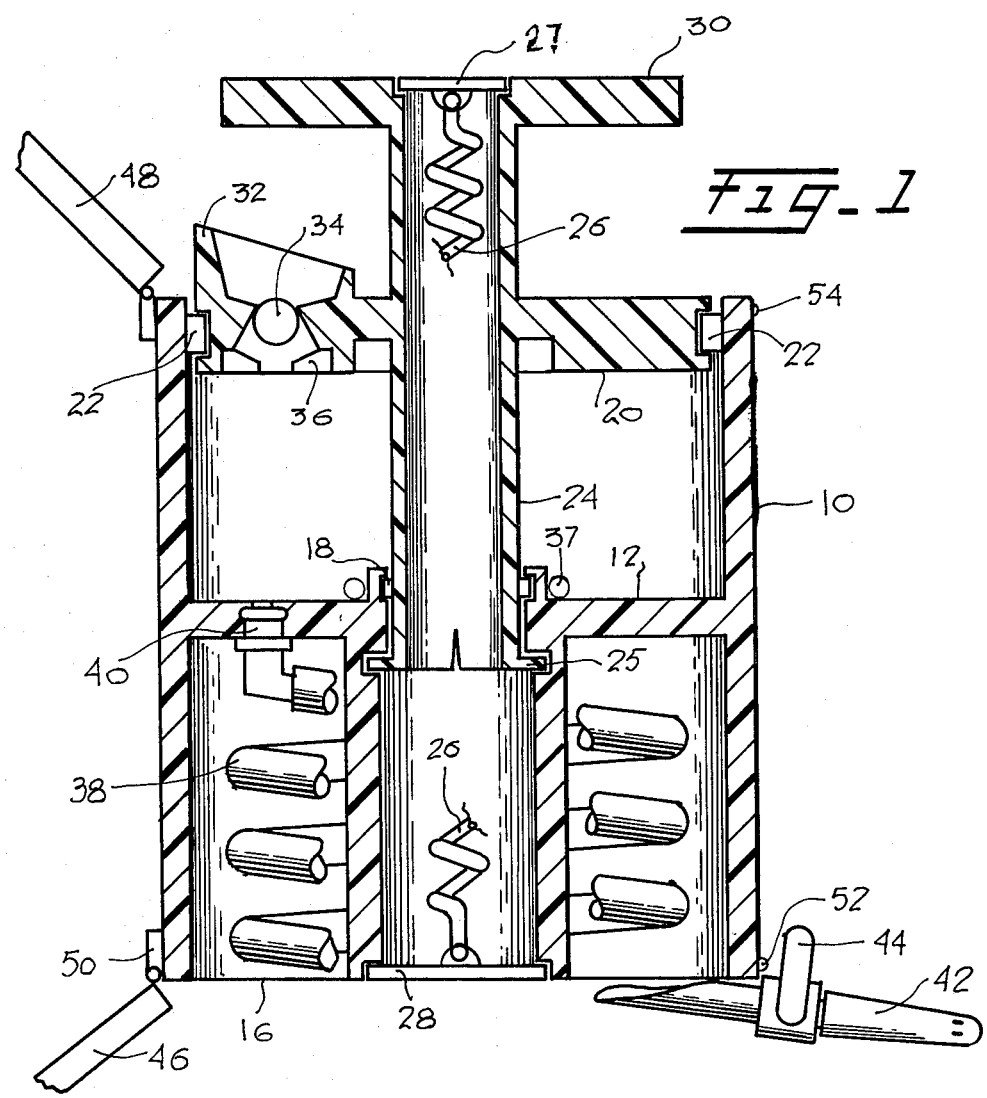
FIG. 1 is a sectional elevation view of the syringe apparatus.

FIG. 1 is a cross-sectional elevation view of the syringe apparatus and illustrates a housing canister 10 which is preferably tubular in shape having the general dimensions of approximately 10 centimeters in diameter and 15 centimeters in length. The canister 10 is preferably formed of a suitable transparent plastic with a circular floor section 12 formed approximately midway between the ends of the canister 10.

As will be subsequently described, the transparent canister 10 permits a convenient viewing of a calibrated tube centrally located in the canister. If desired, the canister may be covered or coated with an ornamental design or color; however, a transparent window should be retained to view the calibrations.

In the preferred embodiment a small thermochromic indicator (not shown) is affixed to the interior wall of the transparent window in the canister 10. The indicator is designed to change color at a fluid temperature very slightly above normal body temperature. A plastic tubular section 14 is connected to the canister floor 12 and is coaxial with the canister 10, extending from the floor 12 to the lower end 16 of the canister. The tubular section 14 may extend slightly above the level of the floor 12 so that its interior surface may conveniently house an annular seal 18 such as an O-ring having an internal diameter of approximately 2.5 centimeters.

Positioned in the cylindrical space above the floor 12 is a piston 20 that has an exterior that generally conforms to the interior surface of the canister 10 and is separated from the canister walls by a suitable seal 22. The piston 20 is preferably suitable plastic material and is formed with a centrally positioned tubular guide 24 that is normal to the surface of the piston and coaxial with the tubular section 14 located in the lower cylinder area below the floor 12. The outside dimension of the tubular guide 24 should be adequate to provide a fluid seal between the guide 24 and the seal 18 in the internal surface of the tubular section 14. The outside surface of the tubular guide 24 is preferably calibrated to provide a convenient and visible measure of fluid in the canister, in ounces and/or milliliters.

A partial ring 25 is formed around the lower end of the tubular guide 24 and forms a part of a bayonet type of latch which, upon a quarter turn of the guide 24, will engage a corresponding groove in the interior wall of the tubular section 14. Thus, the piston 20 may be temporarily latched in a top or extended position to form a cylindrical reservoir between piston 20 and floor 12, and when ready for use, the guide 24 is re-rotated to permit the piston 20 to compress downward.

Figure 2:
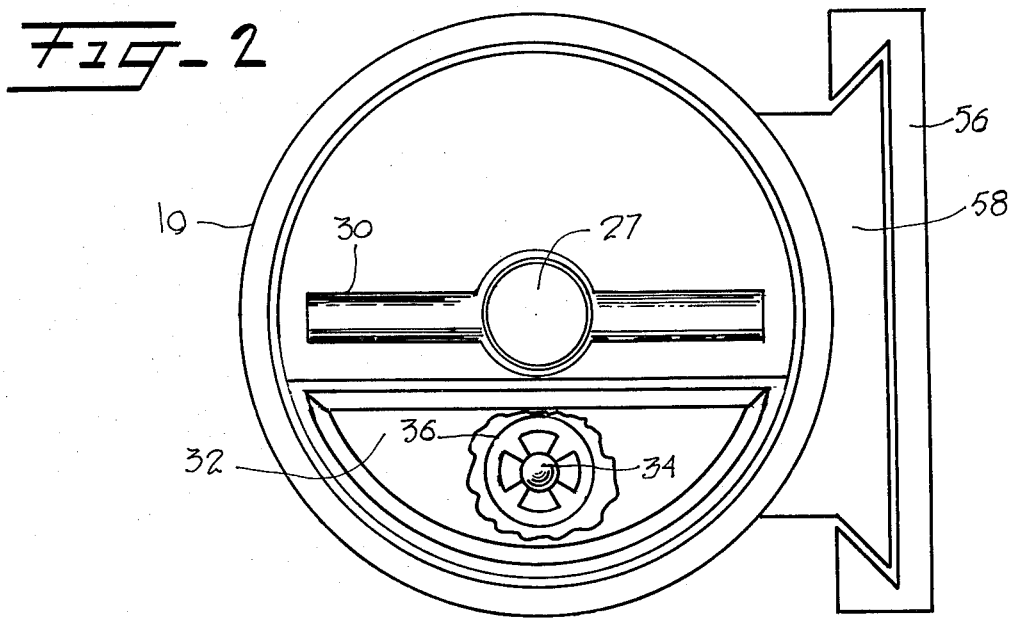
FIG. 2 is a plan view of the apparatus with the top hinged cover removed and with the canister mounted in a wall bracket.

An extension spring 26 is positioned within the bores of the tubular guide 24 and tubular section 14. One end of the spring 26 is connected to a disc cemented in the top end of tubular guide 24 while the second end of the spring 26 is connected to a disc 28 or other suitable fastener mounted in the end of the tubular section 14 adjacent the lower end 16 of the canister 10. Extension spring 26 therefore draws the piston 20 toward contact with the top surface of the canister floor 12 and therefore draws the tubular guide 24 into the bore of the tubular section 14. A piston lift handle 30 is formed in the top surface of the piston 20 to provide a means for lifting the piston in opposition to the extension spring 24. When so lifted to its extended position, the cylindrical reservoir formed between the bottom surface of the piston 20 and the top surface of the floor 12 may be filled with a desired fluid through a relatively large funnel 32 formed in the piston 20 as shown in FIG. 2. In order to insure against loss of fluid when piston 12 is compressed downward, funnel 32 is preferably sealed by a check valve comprising a spherical ball 34 caged in a basket 36 formed in the bottom of the funnel 32 and providing a fluid entrance to the reservoir beneath piston 20.

In the preferred embodiment of the invention, a small, flat, low power heating coil 37 is cemented to the floor 12 of the reservoir to adequately warm the fluid therein. Electrical leads preferably extend through the floor 12 to a power source, but if desired the leads may extend through the side wall of the canister.

Contained within the cylindrical area between the canister floor 12 and the lower end 16 of the canister is a fluid dispensing tubing 38. Tubing 38 is approximately 5 feet in length and is preferably a self-recoiling flexible plastic tubing which, when in its normal coiled condition, conveniently fits within the bore of the canister 10. One end of the tubing 38 is attached to a quick disconnect connector 40 which extends through an opening in the canister floor 12 and into the reservoir formed between the floor 12 and piston 20. The opposite end of the tubing 38 may be provided with a suitable disposable syringe fitting 42 and valve 44 which form no part of this invention.

Both ends of the canister 10 are provided with circular covers 46 and 48. The bottom cover 46 is attached to the bottom side wall surface of the canister by a suitable hinge 50 and when snapped closed over a spring-loaded detent ball 52 extending from the opposite side wall of the canister 10, the cover 46 will retain the coiled tubing 38 within the cylinder formed between the cover and the canister floor 12. A similar top cover 48 may be closed and retained by a spring-loaded detent ball 54 in the top side wall of the canister 10 during storage or whenever piston 20 has been released toward the canister floor 12.

The plan view of FIG. 2 illustrates the syringe apparatus supported by a wall-mounted connector 56. As illustrated in FIG. 2, a flange 58 that is connected to the exterior wall of the canister 10 has a configuration adapted to loosely dovetail into mating portions in the wall connector 56. Thus, if desired, the syringe apparatus may be readily lifted from the connector 56, filled from a convenient water tap or fluid supply, and replaced in the connector. After such use, the apparatus may be conveniently rinsed or flushed, the covers 46 and 48 snapped into their closed position, and the apparatus left mounted relatively inconspicuously in the wall connector if desired.

The operation of the apparatus now becomes apparent. The end covers 46 and 48 are opened, handle 30 is drawn upward against the action of the spring 26 and at the top of the stroke, the handle and tubular guide 24 are rotated a quarter turn to engage the bayonet latch 25. Fluid is then poured through the funnel 32 and check valve 34, 36 to a desired level as indicated by a scale (not shown) on the surface of the guide 24 and observed through the transparent canister 10 and warmed if desired by the heating element 37. When tubing 33 has been removed from the canister and valve 44 opened, the handle 30 is re-rotated to unlatch the bayonet latch 25 and to permit spring 26 to draw down the piston 20 to force the fluid through the tubing 38.

I claim:

1. A hygienic syringe apparatus comprising:
   a canister having a floor positioned approximately midway between the exterior ends of said canister and sealed against the interior of said canister into first and second cylinders;
   a movable piston positioned in said first cylinder and in a plane normal to the longitudinal axis of said canister, said piston extending substantially over the internal cross-sectional area of said first cylinder and separated from the walls of said first cylinder by resilient fluid sealing means;
   compressing means attached to said canister and to said piston for urging said piston toward said canister floor;
   manually operable means on said piston for raising said piston from said floor and for latching said piston in a fixed raised position in said first cylinder;
   a fluid opening in said piston for admitting fluid into said first cylinder; and
   a fluid dispensing tubing located in said second cylinder, one end of said tubing connected to an opening in said conduit floor into said first cylinder.

2. The apparatus claimed in claim 1 wherein said canister is tubular and wherein said canister floor and said movable piston are circular.

3. The apparatus claimed in claim 2 wherein said piston is attached to a tubular guide extending from said piston through said first cylinder and through a tubular section extending through said cylinder.

4. The apparatus claimed in claim 3 further including electrical fluid heating means within said first cylinder.

5. The apparatus claimed in claim 3 wherein said compressing means is a spring.

6. The apparatus claimed in claim 5 wherein said spring extends from said piston through said tubular guide and tubular section to a spring connector in said tubular section and adjacent the end of said second cylinder.

7. The apparatus claimed in claim 6 wherein the space between the exterior surface of said tubular guide and the interior surface of said tubular section are sealed against fluid leakage by an annular fluid seal.

8. The apparatus claimed in claim 7 wherein the top surface of said piston includes a fluid-filling funnel.

9. The apparatus claimed in claim 8 wherein said funnel includes a check valve for preventing the escape of fluid from said first cylinder, said check valve including a caged sealing sphere in a basket section beneath said funnel.

10. The apparatus claimed in claim 9 wherein said canister is provided with hinged releasable covers at each end.

11. The apparatus claimed in claim 10 wherein said fluid dispensing tubing is a flexible self-retracting coiled tubing having a coil diameter substantially corresponding to the inside diameter of said second cylinder.

12. The apparatus claimed in claim 11 wherein said manually operable means on said piston comprises a piston lift handle mounted to the top surface of said piston and a bayonet latch formed in the bottom end of said tubular guide and engageable in a corresponding groove in the interior wall of said tubular section.

13. The apparatus claimed in claim 12 further including mounting means on the exterior surface of said canister, said mounting means being formed to interconnect said apparatus with a wall-mounted connector.

* * * * *